United States Patent [19]

Pistulka

[11] 4,067,751

[45] Jan. 10, 1978

[54] AQUEOUS NACL TEST SOLUTION FOR ALUMINUM AND ITS ALLOYS

[75] Inventor: Wilhelm Pistulka, Burghausen, Germany

[73] Assignee: Vereinigte Metallwerke Ranshofen-Berndorf Aktiengesellschaft, Braunau am Inn, Ranshofen, Austria

[21] Appl. No.: 685,147

[22] Filed: May 11, 1976

[51] Int. Cl.$^2$ .................... C23F 1/02; C20F 11/04; C23G 1/12; C09K 13/00; G01N 33/20
[52] U.S. Cl. .................... 148/6.27; 23/230 C; 73/88 R; 73/89; 73/104; 134/2; 148/6.1; 148/6.14 R; 156/665; 252/79.1; 252/79.5; 252/186; 252/408; 423/272; 423/273
[58] Field of Search ............ 252/186, 79.1, 79.5, 252/408; 23/230 C; 73/88 R, 89, 104; 134/2; 156/20, 22; 423/272, 273; 148/6.1, 6.14 R, 6.27

[56] References Cited

U.S. PATENT DOCUMENTS

| | | | |
|---|---|---|---|
| 2,154,451 | 4/1939 | Hull | 156/20 |
| 2,426,154 | 8/1947 | Reichert et al. | 423/272 |
| 3,019,090 | 1/1962 | Renshaw et al. | 23/230 C |
| 3,316,164 | 4/1967 | Welch, Jr. | 252/79.1 |
| 3,582,282 | 6/1971 | Kampf et al. | 23/230 C |
| 3,652,224 | 3/1972 | Johnson et al. | 23/230 C |
| 3,664,883 | 5/1972 | Henry | 23/230 C |
| 3,685,969 | 8/1972 | Young | 73/88 R |
| 3,869,401 | 3/1975 | Ernst | 252/186 |
| 3,876,381 | 4/1975 | Shaffer et al. | 23/230 C |
| 3,905,907 | 9/1975 | Shiga | 156/20 |

*Primary Examiner*—Benjamin R. Padgett
*Assistant Examiner*—T. S. Gron
*Attorney, Agent, or Firm*—Karl F. Ross

[57] ABSTRACT

A corrosive solution, designed to accelerate the rupture of workpieces of aluminum and its alloys in stress-corrosion-cracking tests, contains sodium chloride, hydrogen peroxide and sodium acetate dissolved in water, with maintenance of an acidic pH.

2 Claims, No Drawings

AQUEOUS NACL TEST SOLUTION FOR ALUMINUM AND ITS ALLOYS

FIELD OF THE INVENTION

My present invention relates to the testing of workpieces of aluminum and aluminum alloys for stress-corrosion cracking and to a treatment bath to be used in such tests.

BACKGROUND OF THE INVENTION

In order to determine the resistance of workpieces to stress-corrosion cracking, numerous specimens must be subjected to a prescribed testing procedure for determining the occurence of cracks due to stress-induced corrosion. Normally, workpieces of aluminum or its alloys take about 100 to 5,000 hours before developing signs of rupture. Because these long test periods are a great inconvenience, it has already been proposed to shorten them by immersing the workpieces under stress in an aqueous solution of sodium chloride, thereby speeding up the developement of detectable faults.

OBJECT OF THE INVENTION

The object of my present invention is to provide an improved treatment bath designed to accelerate significantly the corrosion of aluminum-containing workpieces immersed therein under stress.

SUMMARY OF THE INVENTION

I realize this object, in accordance with the present invention, by the provision of a corrosive treatment bath consisting essentially of an aqueous acidic solution of sodium chloride admixed with hydrogen peroxide, the solution containing the ions of sodium acetate as a buffering agent.

More particularly, the sodium chloride should be present in a proportion ranging between about 0.5% and 5% by weight, the amount of hydrogen peroxide being considerably smaller and ranging preferably between about 0.1% and 1% by weight.

In order to produce the ions of sodium acetate, I dissolve sodium hydroxide and acetic acid in the NaCl solution, with the NaOH generally present in a concentration substantilly exceeding that of the NaCl and with addition of enough $CH_3COOH$ to maintain the pH of the bath at a desired value between 1 and 7.

EXAMPLE

A corrosive treatment bath is prepared with the following composition:

aqueous NaCl solution of 30 grams per liter of water
14 ml $H_2O_2$ per liter
100 ml NaOH (1N) per liter
about 25 ml $CH_3COOH$ (100%) per liter,
yielding a pH of 4

I have found that such a solution will reduce the test period of a workpiece of 90% Al, 9% Zn and 1% Mg to about one-tenth the time required with a conventional 3% NaCl solution, i.e. from some 15 hours to at most 1.5 hours under conditions giving rise to stress-corrosion cracking.

I claim:

1. A method of accelerating stress corrosion cracking of metallic workpieces of aluminum or its alloys for the detection of stress-corrosion cracks therein which comprises immersing said workpieces under stress in a solution consisting essentially of the following ingredients in water:

NaCl in a proportion ranging between substantially 0.5% and 5% by weight;

$H_2O_2$ in a proportion ranging between substantially 0.1% and 1% by weight; and NaOH and $CH_3COOH$ interreacting to produce sodium acetate, said NaOH being present in a concentration substantially exceeding that of the NaCL, said $CH_3COOH$ being present in an amount such that the pH of the solution is maintained between 1 and 7.

2. A method as defined in claim 1 wherein said $CH_3COOH$ is presnt in the solution in an amount establishing a pH of about 4.

* * * * *